United States Patent
Shi

(10) Patent No.: US 9,626,587 B2
(45) Date of Patent: Apr. 18, 2017

(54) ITERATIVE RECONSTRUCTION SCHEME FOR PHASE CONTRAST TOMOGRAPHY

(71) Applicant: Toshiba Medical Systems Corporation, Otawara-shi (JP)

(72) Inventor: Daxin Shi, Vernon Hills, IL (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 163 days.

(21) Appl. No.: 14/471,671

(22) Filed: Aug. 28, 2014

(65) Prior Publication Data

US 2016/0063694 A1    Mar. 3, 2016

(51) Int. Cl.
*A61B 6/00*    (2006.01)
*G06K 9/52*    (2006.01)
*G06K 9/46*    (2006.01)
*G06T 11/00*    (2006.01)
*A61B 6/03*    (2006.01)

(52) U.S. Cl.
CPC .............. *G06K 9/52* (2013.01); *G06K 9/4604* (2013.01); *G06T 11/006* (2013.01); *A61B 6/032* (2013.01); *A61B 6/484* (2013.01); *A61B 6/5205* (2013.01); *G06T 2211/424* (2013.01)

(58) Field of Classification Search
CPC .......................... G21K 2207/005; A61B 6/484; A61B 6/4291; A61B 6/032
See application file for complete search history.

(56) References Cited

U.S. PATENT DOCUMENTS

| 7,180,979 B2 * | 2/2007 | Momose | A61B 6/06 378/62 |
| 2015/0363947 A1 * | 12/2015 | Rigie | G06T 11/005 382/131 |

OTHER PUBLICATIONS

Fu et al., Analysis and accurate reconstruction of incomplete data in X-ray differential phase-contrast computed tomography, Jan. 2014 [retrieved Apr. 14, 2016], Analytical and Bioanalytical Chemistry, vol. 406, Issue 3, pp. 897-904. Retrieved from the Internet: http://link.springer.com/article/10.1007/s00216-013-7482-0.*
Andrei V. Bronnikov, "Phase-Contrast CT: Fundamental Theorem and Fast Image Reconstruction Algorithms," Bronnikov Algorithms, www.bronnikov-algorithms.com, 7 pages, 2006.

(Continued)

*Primary Examiner* — Matthew Bella
*Assistant Examiner* — Dennis Rosario
(74) *Attorney, Agent, or Firm* — Oblon, McClelland, Maier & Neustadt, L.L.P.

(57) ABSTRACT

A method of tomographic imaging the real part of the refractive index of the internal structure of an image volume and a corresponding apparatus for performing the method. The method includes a two-step process of first retrieving phase projections of an image volume from projective intensity measurements through the image volume. The second step of the method includes iterative image reconstruction of an image of the image volume using phase projections taken at multiple projection angles. The first step of intensity measurements and subsequent phase retrieval can use one of many possible phase retrieval methods including the Bronnikov phase retrieval method. The second step of iterative image reconstruction can be performed using the total variation minimization method, the algebraic reconstruction technique method, or any other iterative image reconstruction method.

11 Claims, 9 Drawing Sheets

(56) References Cited

OTHER PUBLICATIONS

Anna Burvall, et al., "Phase retrieval in X-ray phase-contrast imaging suitable for tomography", Optics Express, vol. 19, No. 11, May 11, 2011, (18 pages).
Franz Pfeiffer, et al., "Phase retrieval and differential phase-contrast imaging with low-brilliance X-ray sources", Nature Physics, vol. 2, Mar. 26, 2006, (4 pages).
Thomas Kohler, et al., "Iterative reconstruction for differential phase contrast imaging using spherically symmetric basis functions", Medical Physics Letter, Jul. 21, 2011, (4 pages).
Zhihua Qi, et al., "A Novel Method to Reduce Data Acquisition Time in Differential Phase Contrast Computed Tomography using Compressed Sensing", Medical Imagining 2009: Physics of Medical Imaging, vol. 7258, (8 pages).
Andrei V. Bronnikov, "Theory of quantitative phase-contrast computer tomography", Journal of Optical Society of America A, vol. 19, No. 3, Mar. 2002, (5 pages).
Timm Weitkamp, et al., "X-ray phase imagining with grating interferometer", Optics Express, vol. 13, No. 16, Aug. 8, 2005, (9 pages).
Sheridan C. Mayo, et al., "In-Line Phase-Contrast X-ray Imagining and Tomography for Materals Science", Materials 2012, May 24, 2012, (29 pages).
Max Langer, et al., "Quantitative comparison of direct phase retrieval algorithms in in-line phase tomography", Med. Phys. 35 (10), Sep. 18, 2008, (11 pages).
Emil Y. Sidky, et al., "Accurate image reconstruction from few-views and limited-angle data in divergent-beam CT", Journal of X-Ray Science and Technology 14, 2006, (31 pages).

\* cited by examiner

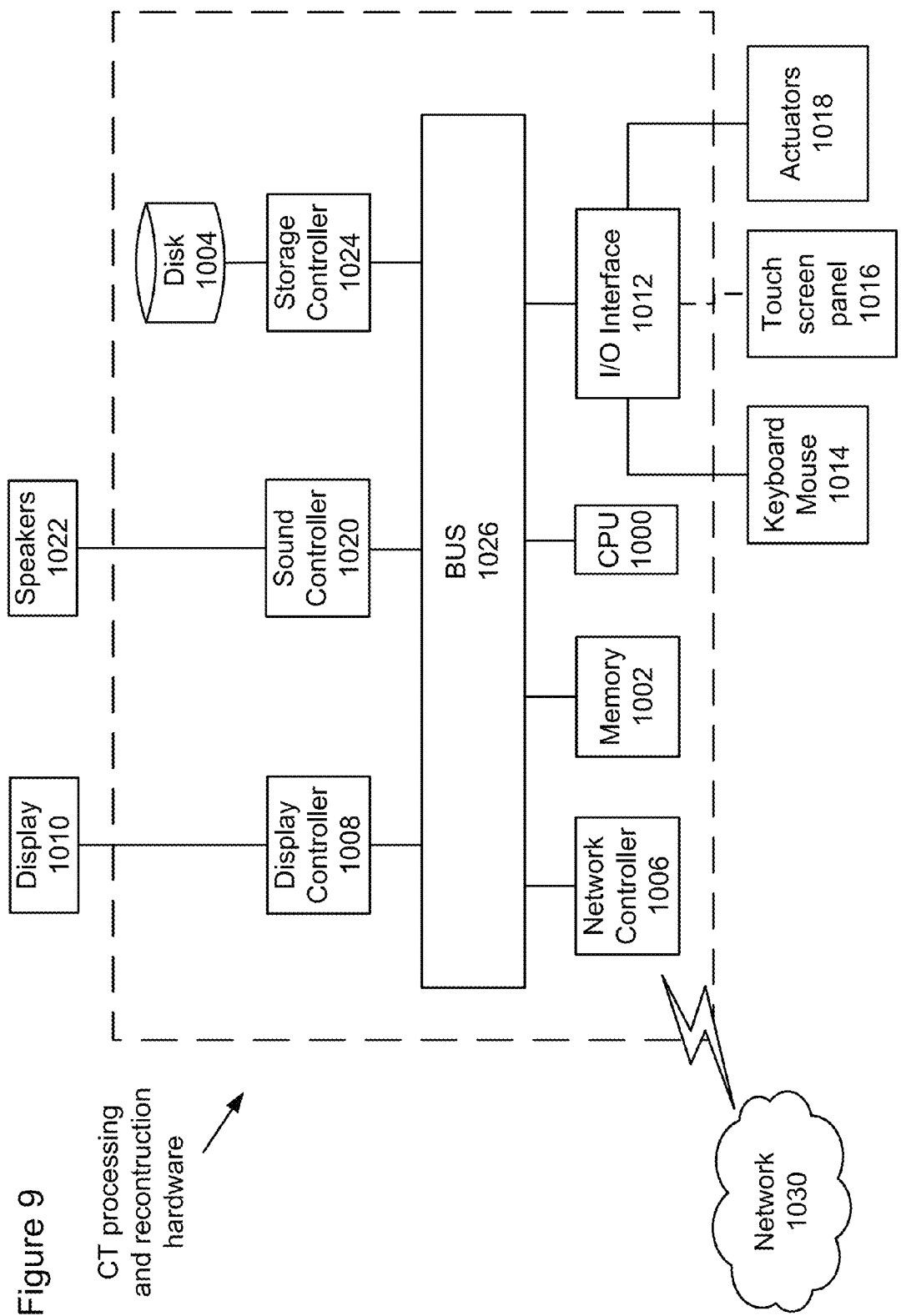

ITERATIVE RECONSTRUCTION SCHEME FOR PHASE CONTRAST TOMOGRAPHY

BACKGROUND

Field

Embodiments disclosed herein relate generally to computed tomography (CT) imaging systems and, more particularly, to CT imaging systems configured to image the real part of the index of refraction of internal structures.

Description of the Related Art

Computed tomography (CT) systems and methods are widely used, particularly for medical imaging and diagnosis. CT systems generally create images of one or more sectional slices through a subject's body. A radiation source, such as an X-ray tube, irradiates the body from one side of the body. A collimator, generally adjacent to the X-ray source, limits the angular extent of the X-ray beam, so that radiation impinging on the body is substantially confined to a planar region defining a cross-sectional slice of the body. At least one detector (and generally many more than one detector) on the opposite side of the body receives radiation transmitted through the body in the plane of the slice, and the attenuation is measured by processing electrical signals received from the detector.

Typically the X-ray source is mounted on a gantry that revolves about a long axis of the body. The detectors are likewise mounted on the gantry, opposite the X-ray source. A single cross-sectional image of the body is obtained by taking projective attenuation measurements at a series of gantry rotation angles, and processing the resultant data using a CT reconstruction algorithm. To obtain multiple cross-sectional images or a three-dimensional image, the X-ray sources and detectors must be translated relative to the body. Either the gantry translates in a direction parallel to the long axis (i.e., perpendicular to the image plane), or the body is translated relative to the gantry. By appropriately rotating the gantry and translating the gantry or the subject, a plurality of views may be acquired, each such view comprising attenuation measurements made at a different angular and/or axial position of the source. In some CT systems, the combination of translation and rotation of the gantry relative to the body is such that the X-ray source traverses a spiral or helical trajectory with respect to the body. The multiple views are then used to reconstruct a CT image showing the internal structure of the slice or of multiple such slices.

Because X-ray CT is the most common form of CT in medicine and various other contexts, the term computed tomography alone is often used to refer to X-ray CT, although other types exist (such as positron emission tomography and single-photon emission computed tomography). Older, less preferred terms that also refer to X-ray CT are computed axial tomography (CAT scan) and computer-assisted tomography.

In one example of X-ray CT, X-ray slice data is generated using an X-ray source that rotates around the object; X-ray sensors are positioned on the opposite side of an image object from the X-ray source. Machines rotate the X-ray source and detectors around a stationary object. Following a complete rotation, the object is moved along its axis, and the next rotation started.

Newer machines permit continuous rotation with the object to be imaged slowly and smoothly slid through the X-ray ring. These are called helical or spiral CT machines. Systems with a very large number of detector rows, such that the z-axis coverage is comparable to the xy-axis coverage are often termed cone beam CT, due to the shape of the X-ray beam (strictly, the beam is pyramidal in shape, rather than conical).

A visual representation of the raw data obtained is called a sinogram, yet it is not sufficient for interpretation. Once the scan data has been acquired, the data must be processed using a form of tomographic reconstruction, which produces a series of cross-sectional images. In terms of mathematics, the raw data acquired by the scanner consists of multiple "projections" of the object being scanned. These projections are effectively the Radon transformation of the structure of the object. Reconstruction, essentially involves solving the inverse Radon transformation.

The technique of filtered back projection is one of the most established algorithmic techniques for this problem. It is conceptually simple, tunable, and deterministic. It is also computationally undemanding, with modern scanners requiring only a few milliseconds per image.

It is also possible to perform tomographic reconstruction problem using linear algebra based on matrix manipulation and matric inversion, but this approach is limited by its high computational complexity. Also, a very high number of projection measurements are required in order for the reconstruction problem not be underdetermined. More recently, manufacturers have developed iterative physical model-based maximum likelihood expectation maximization techniques. These techniques are advantageous because they use an internal model of the scanner's physical properties and of the physical laws of X-ray interactions.

Alternatively, iterative techniques provide images with improved resolution, reduced noise, and fewer artifacts, as well as the ability to greatly reduce the radiation dose in certain circumstances (e.g., reconstruct and image with only a few projections through the image object—often referred to as "few views" image reconstruction). The disadvantage of iterative techniques is they entail a very high computational requirement, but advances in computer technology and high-performance computing techniques, such as use of highly parallel GPU algorithms, now allow practical use.

One well known iterative technique is the Algebraic Reconstruction Technique (ART), also called the Kaczmarz method. This technique is essentially a method for iterative solving the matrix equation $$\vec{g} = M\vec{f},$$

where $\vec{g}$ is a vector that includes all the projection measurement values, $\vec{f}$ is a vector containing the values for the estimated absorption image for the image object, and M is a matrix corresponding to the discretized Radon transform of the X-ray beams passing through the image object. By recognizing that each row vector $\vec{M}_i$ of the matrix M together with the corresponding projection value $g_i$ defines an affine space, an image of the image object can be found through successive affine projections onto the successive affine spaces corresponding to the rows of M. This iterative process converges by using the previous estimate of the image vector $\vec{f}_{m-1}^{\,i}$ to solve for the current image vector estimate $\vec{f}_m^{\,i}$ using the expression $$\vec{f}_m^{\,i} = \vec{f}_{m-1}^{\,i} - \vec{M}_{m-1}(g_{m-1} - \vec{M}_{m-1} \cdot \vec{f}_{m-1}^{\,i}/\vec{M}_{m-1} \cdot \vec{M}_{m-1}),$$

where each iteration progressively estimates $\vec{f}_m^{\,i}$ for $m=2, \ldots, N_{Data}$; $\vec{f}_1^{\,0}$ is the initial guess, and the super script i indicates the $i^{th}$ iteration of affine projections for all values of m. The iterative process until the image estimates converge according to some predefined metric.

Typically, after each iteration through all affine projections a constraint is imposed in order to ensure convergence to a physically meaningful image. For example, in absorption imaging, the image value must be non-negative because a negative absorption value implies gain, which is not physically realistic. Therefore, the final value after each iteration, $\vec{f}_{NData}{}^i$, is subject to a predefined constraint based on a priori knowledge of the image (e.g., no gain), and the constrained final value is then used as the initial value, $\vec{f}_1{}^{i+1}$, for the next iteration of affine projections. Periodically subjecting the image estimates to a predefined constraint is referred to as regularization.

Iterative reconstruction algorithms augmented with regularization can produce high-quality reconstructions for few views and even in the presence of significant noise. For few-view, limited-angle, and noisy projection scenarios, the application of regularization operators between reconstruction iterations seeks to tune the final or intermediate results to some a priori model. For example, enforcing positivity as discussed above is a simple regularization scheme. Minimizing the "total variation" (TV) in conjunction with projection on convex sets (POCS) is also a very popular regularization scheme. The TV-minimization algorithm assumes that the image is predominantly uniform over large regions with sharp transitions at the boundaries of the uniform regions. When the a priori model corresponds well to the image object, these regularized iterative reconstruction algorithms can produce impressive images even though the reconstruction problem is significantly underdetermined (e.g., few view scenarios), missing projection angles, or noisy.

The discussion of CT imaging above has been limited to absorption imaging, wherein the image is for the imaginary part of the index of refraction of the image object. Alternatively, CT imaging can be used to find an image of the real part of the index of refraction using phase contrast CT. Phase contrast CT is also known more generally as phase-contrast X-ray imaging. Phase-contrast X-ray imaging (PCI) is a general term for different technical methods that use information concerning changes in the phase of an X-ray beam that passes through an object in order to create its images. Standard X-ray imaging techniques like radiography or computed tomography (CT) rely on a decrease of the X-ray beam's intensity (attenuation) when traversing the image object, which can be measured directly with the assistance of an X-ray detector. In PCI however, the beam's phase shift caused by the image object is not measured directly, but is transformed into variations in intensity, which then can be recorded by the detector.

In addition to producing projection images, PCI, like conventional transmission, can be combined with tomographic techniques to obtain the 3D-distribution of the real part of the refractive index of the image object. When applied to image objects that consist of atoms with low atomic number Z, PCI is more sensitive to density variations in the image object than conventional transmission-based X-ray imaging. This leads to images with improved soft tissue contrast. For example, for X-rays with an energy of 23 keV, the ratio between phase shift cross section and the absorption cross section for water is $4 \times 10^3$. It is this large difference that is one of the motivations for performing phase contrast imaging, because phase contrast imaging has the potential to deliver contrast that is order of magnitude better than standard absorption images. Phase contrast imaging is especially beneficial for soft tissue, because soft tissues mainly consist of material of low atomic number.

Because X-ray detectors directly measure intensity rather than phase, many techniques have been developed to retrieve phase information from a series of intensity measurements. One technique simply measures the changes in the intensity profile as a function of distance from the image object. Applying diffraction theory to these in-line intensity measurements, it is possible to find the phase of the X-ray beam immediately after the image object. Propagation-based imaging (PBI) is a common name for this technique, but it is also called in-line phase-contrast CT. It consists of an in-line arrangement of an X-ray source, the image object and an X-ray detector, and no other optical elements are required. The primary difference between in-line phase-contrast CT and attenuation based CT is that the detector is not placed immediately behind the image object, but at some distance in order that the radiation beam can evolve identifiable indicia of refraction and diffraction from the image object. This simple setup and the low stability requirement provides a big advantage of this method over other methods, such as crystal interferometers and analyzer based imaging (which are not discussed here).

Under spatially coherent illumination and at an intermediate distance between image object and detector, an interference pattern with "Fresnel fringes" is created. This intermediate distance is referred to as the Fresnel regime and the Fresnel fringes results from free-space propagation for a distance greater than near-field regime, but less than the Fraunhofer Regime, at which intermediate distance the approximation of Kirchhoff's diffraction formula for the Fresnel diffraction equation is valid. In contrast to crystal interferometry the recorded interference fringes in PBI are not proportional to the phase itself, but to the second derivative (the Laplacian) of the phase of the wavefront. Therefore the method is most sensitive to abrupt changes in the decrement of the refractive index. This leads to stronger contrast outlining the surfaces and structural boundaries of the image object (edge enhancement) compared with a conventional radiogram.

Differential phase-contrast imaging is a second phase-contrast imaging method. Differential phase-contrast imaging uses Talbot interference from a series of two diffraction gratings. For this reason it is sometimes referred to as Grating-based imaging (GBI), shearing interferometry, or X-ray Talbot interferometry (XTI). The standard method for differential phase-contrast imaging consists of a phase grating and an analyzer grating.

The technique is based on the Talbot effect or "self-imaging phenomenon," which is a Fresnel diffraction effect and leads to repetition of a periodic wavefront after a certain propagation distance, called the "Talbot length." This periodic wavefront can be generated by spatially coherent illumination of a periodic structure, like a diffraction grating, and if so the intensity distribution of the wave field at the Talbot length resembles exactly the structure of the grating and is called a self-image. It has also been shown that intensity patterns will be created at certain fractional Talbot lengths. At half the distance the same intensity distribution appears, except for a lateral shift of half the grating period, while at certain smaller fractional Talbot distances the self-images have fractional periods and fractional sizes of the intensity maxima and minima, which become visible in the intensity distribution behind the grating, a so-called Talbot carpet. The Talbot length and the fractional lengths can be calculated by knowing the parameters of the illuminating radiation and the illuminated grating and thus gives the exact position of the intensity maxima, which needs to be measured in GBI.

In differential phase-contrast imaging, a image object is placed before the phase grating and thus the interference pattern of the Talbot effect is modified by absorption, refraction and scattering in the image object. For a phase object with a small phase gradient the X-ray beam is deflected by $$\Delta\alpha = \frac{1}{k}\frac{\partial\varphi(x)}{\partial x}$$

where k is the length of the wave vector of the incident radiation and the second factor on the right-hand side is the first derivative of the phase in the direction perpendicular to the propagation direction and parallel to the alignment of the grating. Since the transverse shift of the interference fringes is linearly proportional to the deviation angle of the differential phase of the wave front is measured in GBI. In other words, the angular deviations are translated into changes of locally transmitted intensity. By performing measurements with and without the image object, the change in position of the interference pattern caused by the image object can be retrieved.

Two different methods can be used to retrieve the differential phase using GBI. In the first method, phase information is separated from the other contributions to the signal using a technique called "phase-stepping." See T. Weitkamp, et al., *X-ray phase imaging with a grating interferometer*, Opt. Express 13, p. 6296 (2005), incorporated herein by reference in its entirety. See also, M. Nilchaian et al., *Fast iterative reconstruction of differential phase contrast X-ray tomograms*, Opt. Express 21, p. 5511 (2012), incorporated herein by reference in its entirety.

In the second method, Moiré fringes are used to retrieve the differential phase. See A. Momose, et al., *High-speed X-ray phase imaging and X-ray phase tomography with Talbot interferometer and white synchrotron*, Opt. Express 17, p. 12540 (2009), incorporated herein by reference in its entirety. See also, N. Bevins et al., *Multicontrast X-ray computed tomography imaging using Talbot-Lau interferometry without phase stepping*, Med. Phys 39, p. 424 (2012)), incorporated herein by reference in its entirety.

With both of these phase-extraction methods, tomography is applicable by rotating the image object around the tomographic axis, recording a series of images with different projection angles and using back projection algorithms to reconstruct the 3-dimensional distributions of the real and imaginary parts of the refractive index.

In contrast to the differential phase contrast CT based on GBI, which requires determination of the phase in order to perform tomographic reconstruction of the index of refraction image, an exact analytic reconstruction formula has been developed for in-line phase contrast tromography by Bronnikov. See A. V. Bronnikov, *Theory of quantitative phase-contrast computed tomography*, JOSA A, 19, p. 472 (2002), incorporated herein by reference in its entirety. This single-step phase contrast CT processing method enables reconstruction of an image of the real part of the index of refraction directly from intensity measurements. The Bronnikov reconstruction formula is given by $$f(x, y, z) = \frac{1}{4\pi^2}\int_0^\pi d\varphi \mathcal{F}_2^{-1}\left\{\frac{|v_y|\hat{g}(v_{x'}, v_{y'}, \varphi)}{v_x^2 + v_y^2}\right\}$$

-continued where $$\hat{g}(v_{x'}, v_y, \varphi) = \frac{1}{d}\mathcal{F}_2\left\{\frac{I_\varphi^{z=d}(x', y')}{I_\varphi^{z=0}(x', y')} - 1\right\}$$

and $I_\phi^z(x', y')$ is the radiation intensity along the x'y' plan at location z. Here, $\mathcal{F}_2\{\bullet\}$ and $\mathcal{F}_2^{-1}\{\bullet\}$ are respectively the two-dimensional Fourier transform and the inverse two-dimensional Fourier transform. If the image object is a pure phase object, then $I_\phi^{z=0}(x', y')$ is independent of whether or not the image object is present. Therefore, $I_\phi^{z=0}(x', y')$ should already be known based on calibration measurements taken before the image was placed in the radiation path, and thus only $I_\phi^{z=d}(x', y')$ needs to be measured. Otherwise, if the image object is a mixed phase/absorption object both $I_\phi^{z=0}(x', y')$ and $I_\phi^{z=d}(x', y')$ need to both be measured in order to reconstruct an image of the real part of the index of refraction.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 9 shows an embodiment of computer hardware for performing a two-step phase contrast tomography method.

DETAILED DESCRIPTION

Figure 1:
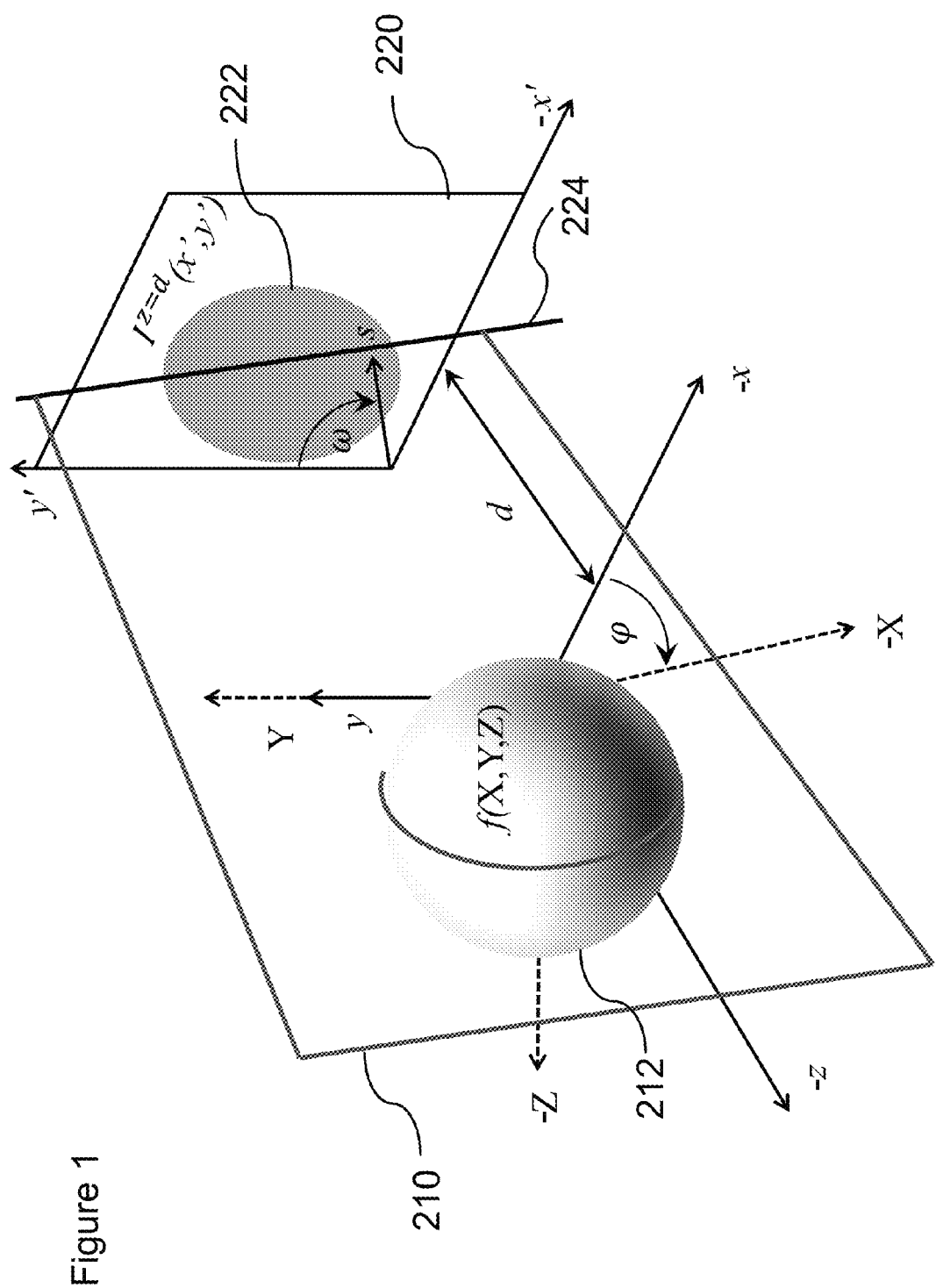
FIG. 1 shows the arrangement of a projective measurement of an image object onto a detector plan.

In one embodiment, the present disclosure provides a method for computer aided imaging comprising: obtaining intensity data that indicates an intensity of radiation at a detector array, wherein the radiation has propagated through an image volume, the intensity data is obtained for the radiation propagating in a plurality of projection angles through the image volume, and the intensity data indicates the radiation intensity at a plurality of distances from the image volume; determining a phase of the radiation for each of the plurality of projection angles at a first boundary immediately adjacent to the image volume, wherein the phase is determined using a phase retrieval method; and reconstructing an image of a real part of an index of refraction of the image volume using an iterative reconstruction algorithm, where the iterative reconstruction algorithm includes the step of an performing an affine projection of an image vector onto an radon transform affine space, where the radon transform affine space is determined by a value of the intensity data and a radon transform for a propagation ray of the radiation that corresponds to the value of the intensity data, and the image vector is an approximation of the image of the real part of the index of refraction of the image volume.

In one aspect, the present disclosure provides the radiation is X-ray radiation.

In one aspect, the present disclosure provides that the radiation beam is a colimated beam with parallel rays.

In one aspect, the present disclosure provides that the radiation beam is a divergent beam configured in a cone beam.

In one aspect, the present disclosure provides that the radiation beam is a divergent beam configured in a fan beam.

In one aspect, the present disclosure provides that the phase retrieval method is a method taken from the group consisting of the transport intensity equation algorithm, the contrast transfer function algorithm, the mixed transport-intensity-equation/contrast-transfer-function algorithm, the Bronnikov algorithm, the modified Bronnikov algorithm, the phase-attenuation duality algorithm, the single material algorithm, the two materials algorithm, the Fourier method with Born approximation method algorithm, and the Fourier method with Rytov approximation algorithm.

In one aspect, the present disclosure provides that the reconstruction algorithm is taken from the group consisting of an algebraic reconstruction technique algorithm, a total variation minimization method algorithm, a simultaneous iterative reconstruction algorithm, an iterative least squares technique algorithm, and a simultaneous algebraic reconstruction technique algorithm.

In one aspect, the present disclosure provides that the phase and amplitude of the radiation at the first boundary of the image volume is determined using differential phase contrast computed tomography, where the plurality of rays traverse a series of two diffraction gratings that are separated by a predetermined fraction of the Talbot length.

In one embodiment, the present disclosure provides an apparatus comprising: circuitry configured to intensity data that indicates an intensity of radiation at a detector array, wherein the radiation has propagated through an image volume, the intensity data is obtained for the radiation propagating in a plurality of projection angles through the image volume, and the intensity data indicates the radiation intensity at a plurality of distances from the image volume; circuitry configured to determine a phase of the radiation for each of the plurality of projection angles at a first boundary immediately adjacent to the image volume, wherein the phase is determined using a phase retrieval method; and circuitry configured to reconstruct an image of a real part of an index of refraction of the image volume using an iterative reconstruction algorithm, where the iterative reconstruction algorithm includes the step of an performing an affine projection of an image vector onto an radon transform affine space, where the radon transform affine space is determined by a value of the intensity data and a radon transform for a propagation ray of the radiation that corresponds to the value of the intensity data, and the image vector is an approximation of the image of the real part of the index of refraction of the image volume.

It is well known that diffraction patterns can be categorized into three regions: the "near-field" region, the Fresnel region, and the Fraunhofer region. Assuming that a mixed phase-and-amplitude object having characteristic length D is positioned at z=0, a uniform wavefront of wavelength $\lambda$ propagating in the positive z direction will first pass through the object. After passing through the object, the wavefront evolves as it propagates first through the near-field region (e.g., $z < D^2/\lambda$), then through the Fresnel region (e.g., $z \sim D^2/\lambda$), and finally through the Fraunhofer region (e.g., $z > D^2/\lambda$). Immediately after passing through the object at z=0, only the absorption profile of the object is observed in the intensity profile of the wave. As the wavefront propagates into the "near-field" region (i.e., $z < D^2/\lambda$, where D is a characteristic length of the image object and $\lambda$ is the wavelength of the radiation) interference fringes (also known as diffraction rings) begin to form in regions where there is a sharp change in the phase (i.e., where the second derivative of the phase is non-zero). In the near field region, these interference fringes are sometimes referred to as edge enhancement, and the intensity profile in the near field is given by $$I_\varphi^{z=d}(x', y') \approx I_\varphi^{z=0}(x', y')\left(1 - \frac{\lambda d}{2\pi}\nabla^2 \Phi(x', y')\right),$$

where $\Phi(x', y')$ is the phase, and d is the distance between the image object and the image plane. Thus, in the near field the phase can be found as $$\Phi(x', y') \approx -\frac{2\pi}{\lambda d}\nabla^{-2}\left(\frac{I_\varphi^{z=d}(x', y')}{I_\varphi^{z=0}(x', y')} - 1\right).$$

Recognizing that the inverse Laplacian can be expressed in terms of Fourier transforms as $$\nabla^{-2} = -\frac{1}{4\pi^2}\mathcal{F}_2^{-1}\frac{1}{v_{x'}^2 + v_{y'}^2}\mathcal{F}_2,$$

where the Laplacian is taken in only the x' and y' directions, $\mathcal{F}_2^{-1}$ and $\mathcal{F}_2$ are the inverse two-dimensional Fourier transform and the two-dimensional Fourier transform, respectively, and $v_{x'}$ and $v_{y'}$ are the spatial frequencies corresponding respectively to x' and y'. Therefore, in the near field, where $z \ll D^2/\lambda$, the phase of a wavefront can be retrieved from a series of intensity measurements at z=0 and z=d using the expression $$\Psi(x', y', \Phi_i) = \frac{1}{2\pi\lambda}\mathcal{F}_2^{-1}\left\{\frac{\hat{g}_\varphi(v_{x'}, v_{y'})}{v_{x'}^2 + v_{y'}^2}\right\},$$

where $\hat{g}_\phi(v_x, v_y, \phi) = \mathcal{F}_2\{g_\phi(x', y')\}$, and $$g_\phi(x', y') = \frac{1}{d}\left(\frac{I_\phi^{z=d}(x', y')}{I_\phi^{z=0}(x', y')} - 1\right).$$

The above method of phase retrieval is often referred to as the Bronnikov phase retrieval method. It is also noted that the above expression for the phase retrieval is very similar to the expression inside the integral for the Bronnikov reconstruction formula. Also, it is noted that the outer integral of the Bronnikov reconstruction formula is very similar to a back projection operator, which is a method for solving the inverse Radon transformation problem.

Figure 2:
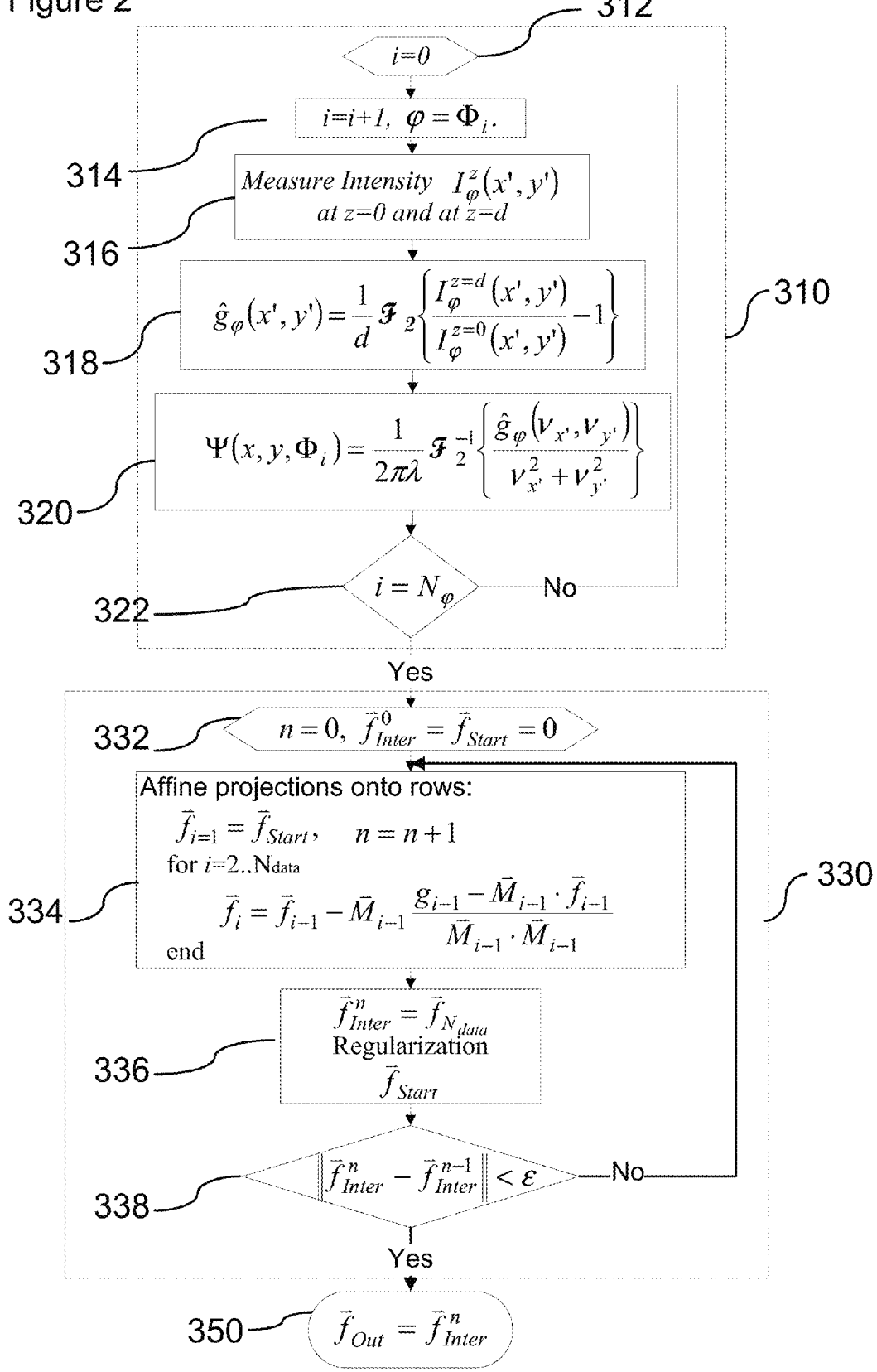
FIG. 2 shows a flowchart diagram of a two-step phase contrast tomography method for retrieving phase projections and iterative image reconstruction of the real part of the index of refraction.

Referring now to the drawings, wherein like reference numerals designate identical or corresponding parts throughout the several views, FIG. 1 shows the geometry of a projective measurement for phase-contrast CT imaging. An image object 212 having a real part of the index of refraction given by the function $f(X,Y,Z)$ is positioned with an image volume. A highly coherent X-ray beam propagates along the z-axis, which is at an angle $\phi$ relative to the Z-axis. Multiple projection images are taken at several different projection angles $\phi$. In each projection image the X-rays pass through the image object and continue to propagate until the X-rays impinge a detector plane 220. The detector plane 220 will include an array of pixels to detect the X-ray intensity at discrete locations across the detector plane 220. These measurements give rise to a map of the intensity $I_\phi^{z=d}(x', y')$ across the detector, which is recorded into computer memory storage and later processed to create a CT image of the image object 212. In FIG. 2 the detector 220 is shown to be a distance d from the closest boundary of the image volume.

In FIG. 1, the detector plane 220 is a two-dimensional plane. In an alternative embodiment, the detector can be one-dimensional detector array 224 and the X-ray beam can be a long and narrow "pencil" beam. These one-dimensional projections are disadvantageous for phase contrast imaging because one-dimensional projections only provide interference fringes along a single dimension (i.e., the long axis of the detector and beam). Therefore, in order to obtain a three-dimensional phase-contrast image while using one-dimensional projection measurements, for a given projection angle each image pixel in the two-dimensional pixel array should be measured twice, once at each of two orthogonal orientations of the pencil beam (e.g., one measurement where $\omega=0°$ and one measurement where $\omega=90°$, where $\omega$ is the angle of the detector relative to the y'-axis of the image plane).

In the interest of simplicity and concreteness, only the case of parallel X-ray beams is discussed here. However, one of ordinary skill in the art would recognize that cone X-ray beams and fan X-ray beams can also be used. Also, X-ray beams that are not perfectly collimated can be used, so long as the X-ray beam has a sufficiently high degree of spatial coherence.

Also, this technique is not limited to X-ray beams. Any type of radiation or other type of wavefront with a sufficiently high degree of spatial coherence can be used to image the real part of the index of refraction of an image object 212 using the proposed imaging method presented here.

Based on the abovementioned similarities between the inner integrals of the Bronnikov reconstruction formula and the near-field phase retrieval and the similarities between the outer integral of the Bronnikov reconstruction formula and the inverse Radon transform via back projections, the proposed algorithm applies a two-step process that is analogous to first performing the inner integrals of the Bronnikov reconstruction formula as the first step and then performing the outer integral of the Bronnikov reconstruction formula Bronnikov reconstruction formula as the second step.

The first step in the two-step process is to retrieve the phase of a radiation wavefront using a phase retrieval method such as the Bronnikov phase retrieval method. This phase retrieval is performed by making a series of intensity measurements at various distances from the image object 212 and then using the Bronnikov phase retrieval method or any other related method for phase retrieval. The Bronnikov phase retrieval method assumes the intensity measurements were performed in the near field, whereas other phase retrieval methods, such as the contrast transfer method, relax this assumption while imposing other assumptions. Depending on the particulars of a given imaging problem, one phase retrieval method may be favored over the rest because the underlying assumptions of the phase retrieval method conform more closely to the given parameters of the imaging problem. A discussion of the underlying assumptions of several phase retrieval methods can be found in A. Buvall, et al., *X-ray phase contrast imaging suitable for tomography*, Opt. Express 19, 10359 (2011), incorporated herein by reference in its entirety. Specifically, A. Buvall, et al. discusses the Bronnikov phase retrieval method method and six other phase retrieval method including the assumptions for each phase retrieval method. Similarly, M. Langer, et al., *Quantitative comparison or direct phase retrieval algorithms in in-line phase tomography*, Med. Phys., 35, 4556 (2008), incorporated herein by reference in its entirety, discusses the Bronnikov phase retrieval method and three other phase retrieval method including the assumptions for each phase retrieval method.

The second step in the proposed two-step phase-contrast CT method uses an iterative reconstruction algorithm to obtain an image of the real part of the index of refraction for the image object 212. There are many iterative CT reconstruction algorithms and any of these algorithms can be used depending on such factors as a priori knowledge about the image object and knowledge of the projective imaging system. For example, the total variation (TV) minimization algorithm is popular for imaging the soft matter commonly encountered in various organs. This algorithm assumes a priori knowledge that the tomographic images are relatively constant over extended volumes (e.g., the region occupied by an organ), and rapid variations in the image occur primarily at the boundaries of internal structures (e.g., at the boundaries between organs). Therefore the TV-minimization algorithm seeks to impose conditions that reinforce this structure by minimizing the $l_1$-norm on the gradient of the tomographic images. The steps of the TV-minimization algorithm are mostly identical to the ART algorithm discussed above, except that the regularization in the TV-minimization algorithm minimizes the $l_1$-norm on the gradient of the tomographic images. Details of the TV-minimization algorithm can be found in E. Sidky, et al., *Accurate image reconstruction from few-views and limited-angle data in divergent beam CT*, J Xray Sci Technol, 14, 119 (2008), incorporated herein in its entirety by reference.

One advantage of the TV minimization algorithm is that it has been demonstrated to produce high quality tomographic images with much fewer projection images compared with filtered back projection image reconstructions.

As an alternative embodiment, one of ordinary skill in the art will recognize that there are other regularization methods besides those already mentioned of imposing non-negativity on the tomographic images and the regularization method that minimizes the $l_1$-norm of the gradient of the tomographic images. Thus, one of ordinary skill in the art will recognize that other regularization methods can be used in the iterative tomographic image reconstruction.

FIG. 2 shows a flowchart of one embodiment of the proposed phase-contrast CT imaging method. In this embodiment the method is subdivided into two parts—the phase projection loop 310 and the iterative tomographic image reconstruction loop 330.

The phase projection loop 310 acquires phase projections of the image object 212 at projection angles $\phi = \Phi_i$ where $i = 1 \ldots N_\phi$ for a total of $N_\phi$ unique phase projections.

The first step 314 in the phase projection loop 310 increments the loop variable i and sets the current projection angle $\phi$ to the angle $\Phi_i$.

The second step 316 in the phase projection loop 310 consists of measuring the intensity projections onto detector plane 220 located at z=0 and onto the detector plane 220 when it is located at z=d. If the image object 212 is a pure phase object (i.e., the image object 212 does not absorb X-rays), then the intensity measured at z=0 will always be identical to the X-ray beam intensity in the absence of an image object. In this case the intensity measurements simplify to a single measurement of $I_\phi^{z=d}(x', y')$, and the measurement of $I_\phi^{z=0}(x', y')$ can be obtained from a previous calibration measurement taken in the absence of the image object 212.

The third step 318 in the phase projection loop 310 consists of calculating the quantity $\hat{g}_\phi(v_{x'}, v_{y'}, \phi)$ from the measured intensities $I_\phi^{z=d}(x', y')$ and $I_\phi^{z=0}(x', y')$, where $$g_\phi(x', y') = \frac{1}{d}\mathcal{F}_2\left\{\frac{I_\phi^{z=d}(x', y')}{I_\phi^{z=0}(x', y')} - 1\right\}.$$

The fourth step 320 in the phase projection loop 310 consists of calculating the phase projection $\Psi(x', y', \Phi_i)$ from $\hat{g}_\phi(v_{x'}, v_{y'}, \phi)$, where $$\Psi(x', y', \Phi_i) = \frac{1}{2\pi\lambda}\mathcal{F}_2^{-1}\left\{\frac{\hat{g}_\phi(v_{x'}, v_{y'})}{v_{x'}^2 + v_{y'}^2}\right\}.$$

The phase projection loop 310 is repeated $N_\phi$ times in order to obtain $N_\phi$ unique phase projections at different projection angles.

After completing the phase projection loop 310, the iterative tomographic image reconstruction loop 330 is performed. All of the phase projection values $\Psi(x', y', \Phi_i)$ are arranged into a vector $\vec{g}$ with components $g_n$ and a matrix M with components $M_{n,m}$ is defined such that each row vector $\vec{M}_n$ is the discretized radon transform corresponding to the projection value $g_n$.

The first step 332 of the image reconstruction loop 330 is to initialize a tomographic image vector $\vec{f}_{start}$ and the intermediate tomographic image vector $\vec{f}_{Inter}^{n=0}$ to zero. Alternatively, these vectors can be initialized to any other value including using the filtered back projection method, the Bronnikov analytical expression given above, or some other method to estimate an image of the image object 212.

The second step 334 of the image reconstruction loop 330 performs affine projections onto the rows of the discretized radon transform matrix M, where the input vector for the current affine projection $\vec{f}_i$ results from the projection of $\vec{f}_{i-1}$ onto the affine space corresponding to $\vec{M}_{i-1}$ and $g_{i-1}$, where $$\vec{f}_i = \vec{f}_{i-1} - \vec{M}_{i-1}(g_{i-1} - \vec{M}_{i-1} \cdot \vec{f}_{i-1} / \vec{M}_{i-1} \cdot \vec{M}_{i-1}).$$

The third step 336 of the image reconstruction loop 330 performs the chosen regularization method (e.g., the TV minimization algorithm) on the current intermediate tomographic image vector $\vec{f}_{Inter}^n$, where $\vec{f}_{Inter}^n = \vec{f}_{i=Ndata}$. The value of the start tomographic image vector $\vec{f}_{Start}$ for the next loop is then set to the result of the regularization method.

The loop then repeats until the image estimate $\vec{f}_{Inter}^n$ satisfies a predefined convergence criteria, e.g., when difference between the current tomographic image $\vec{f}_{Inter}^n$ and previous tomographic image $\vec{f}_{Inter}^{n-1}$ reduces below a predefined threshold.

The final step 350 of the two-step phase contrast imaging method is setting the final tomographic image $\vec{f}_{Out}$ to be equal to the intermediate tomographic image $\vec{f}_{Inter}^n$ from the final iteration of the image reconstruction loop 330.

FIGS. 3-7 show an example of how the proposed method using the TV minimization algorithm compares with the Bronnikov reconstruction formula for image reconstruction, and especially how the two methods compare for the case where there are only a few projection views. The few-view scenario is important because fewer views can result in a lower dosage of radiation to the patient.

Figure 3:
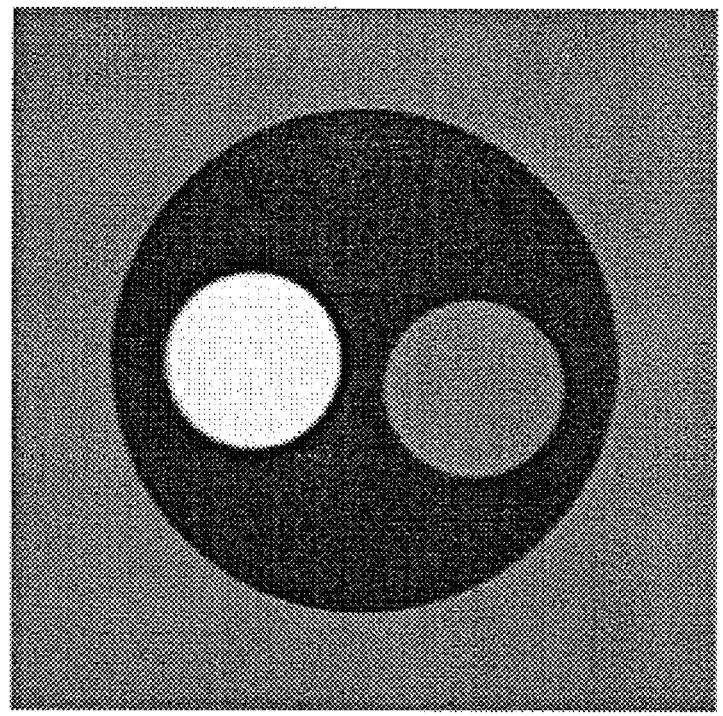
FIG. 3 shows the real part of the index of refraction of a an image object.

FIG. 3 shows an example of an image object, where grey indicates an index of refraction of 1, white indicates an index of refraction greater than 1 and black indicates an index of refraction less than one. The index of refraction is the real part of the index of refraction, unless explicitly stated otherwise. In FIGS. 3-7, the imaginary part of the index of refraction is assumed to be zero. Thus, this example considers only the case of a pure phase object.

Figure 4:
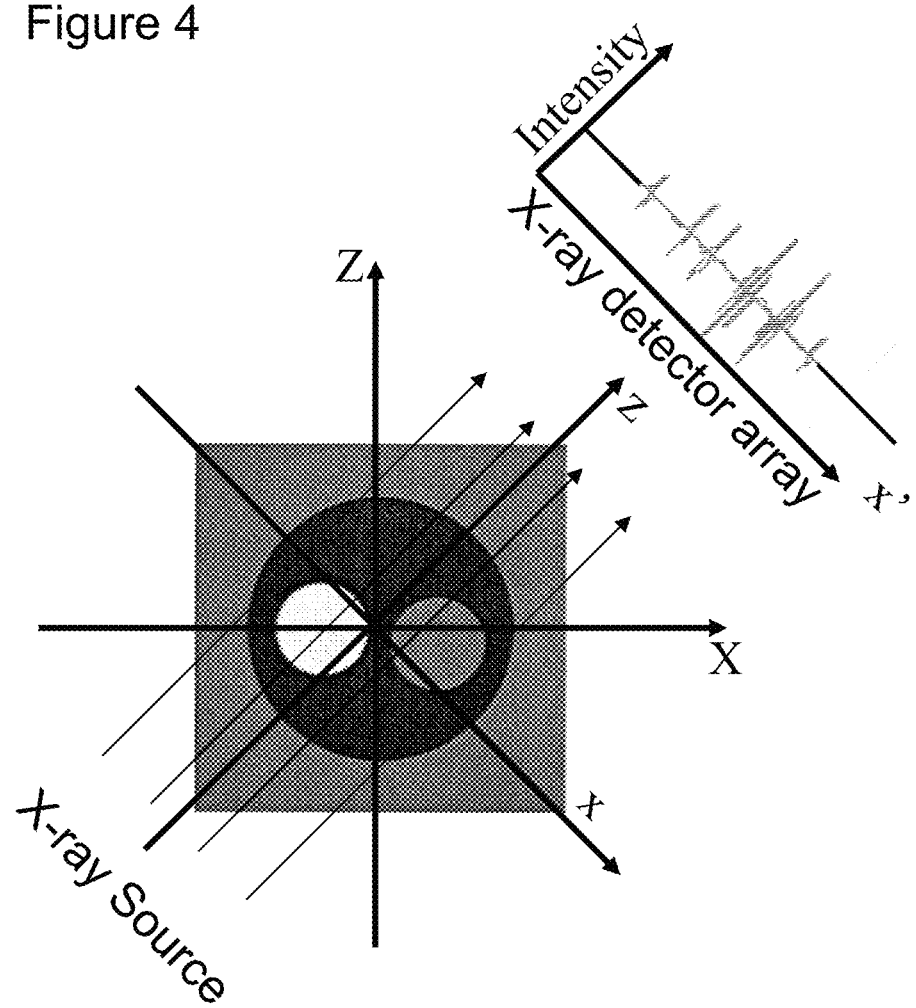
FIG. 4 shows a diagram of a projective measurement of a an image object.

FIG. 4 shows the arrangement for a projection image. The X-rays propagate from the source through the image object until the X-rays are absorbed by the detector array at z=d. The intensity measurement is registered on the detector array, and the intensity measurement is then read and recorded into a computer memory where it is stored for later processing.

Figure 5:
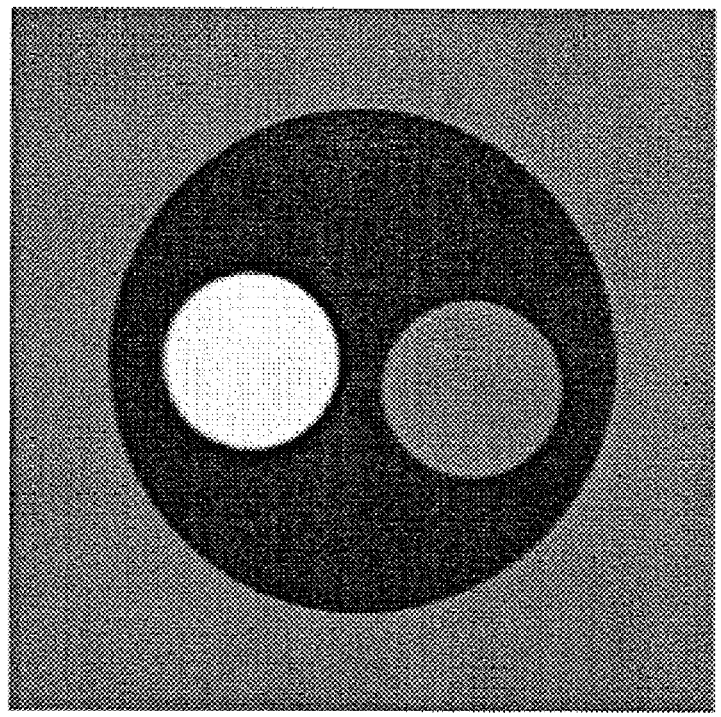
FIG. 5 shows a reconstruction of the real part of the index of refraction of an image object using the Bronnikov reconstruction formula with 256 projections.

FIG. 5 shows the reconstructed image of the index of refraction using the Bronnikov reconstruction formula with 256 projections. Comparing FIG. 5 with FIG. 3, it can be seen that the reconstructed image is consistent with the image object. However, as the number of projections decreases the reconstructed image becomes poorer.

Figure 6:
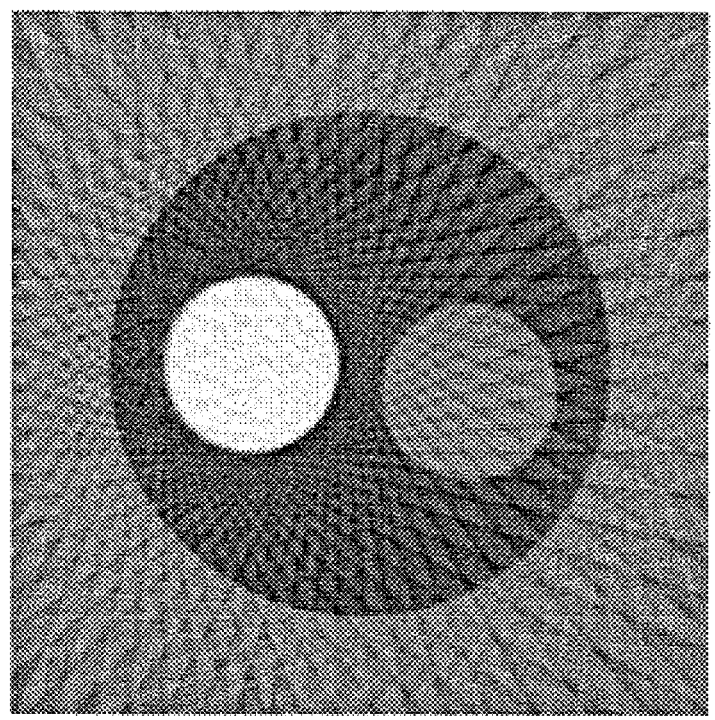
FIG. 6 shows a reconstruction of the real part of the index of refraction of an image object using the Bronnikov reconstruction formula with 32 projections.

FIG. 6 shows the reconstructed image of the index of refraction using the Bronnikov reconstruction formula with 32 projections. Streaks are present in the reconstructed image, similar to those streaks found in more conventional absorption-based CT for the case of filtered back projections using only a few projection views.

Figure 7:
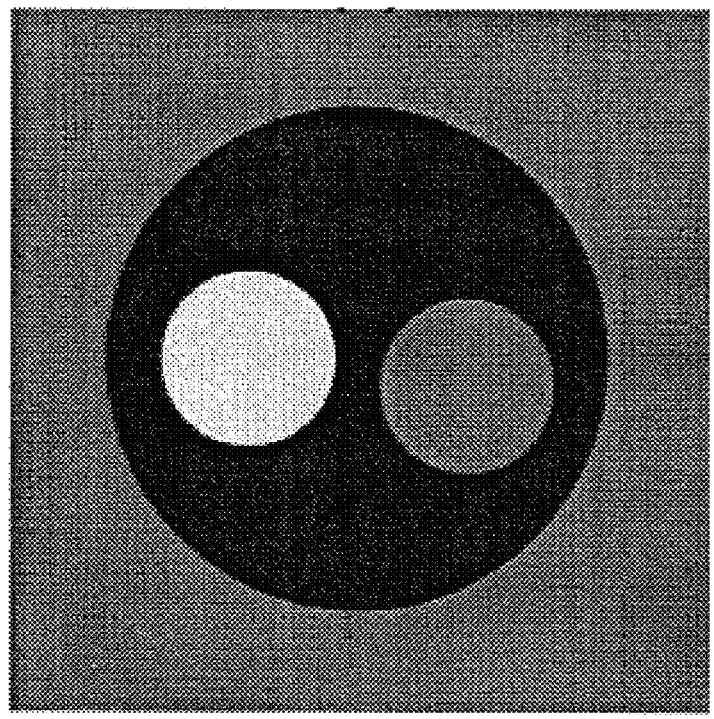
FIG. 7 shows a reconstruction of the real part of the index of refraction of an image object using the two-step phase retrieval iterative image reconstruction method with 32 projections.

FIG. 7 shows the reconstructed image created by using the proposed method with the TV minimization algorithm and only 32 projections. Comparing FIG. 7 with FIG. 3 and with FIG. 5, it is observed that, with far fewer projections, the disclosed method achieves similar image quality to a Bronnikov reconstruction formula that uses almost 10 times the number of projections.

In FIGS. 3-7, the Bronnikov phase retrieval method (also called the Bronnikov phase retrieval algorithm) has been used for the phase retrieval step in the two-step phase contrast CT method. In alternative embodiments, other phase retrieval methods can be used. In many imaging scenarios, these alternative phase retrieval methods may be preferable to the Bronnikov phase retrieval method depending on the parameters of the imaging scenario. Conventional phase retrieval methods include the transport intensity equation algorithm, the contrast transfer function algorithm, the mixed transport-intensity-equation/contrast-transfer-function algorithm, the Bronnikov algorithm, the modified Bronnikov algorithm, the phase-attenuation duality algorithm, the single material algorithm, the two materials algorithm, the Fourier method with Born approximation method algorithm, and the Fourier method with Rytov approximation algorithm. In many of these phase retrieval methods, the intensity profile has to be measured at multiple distances from the image object 212, where the image positions are different than the z=d and z=0 image positions used in the Bronnikov phase retrieval algorithm.

Figure 8:
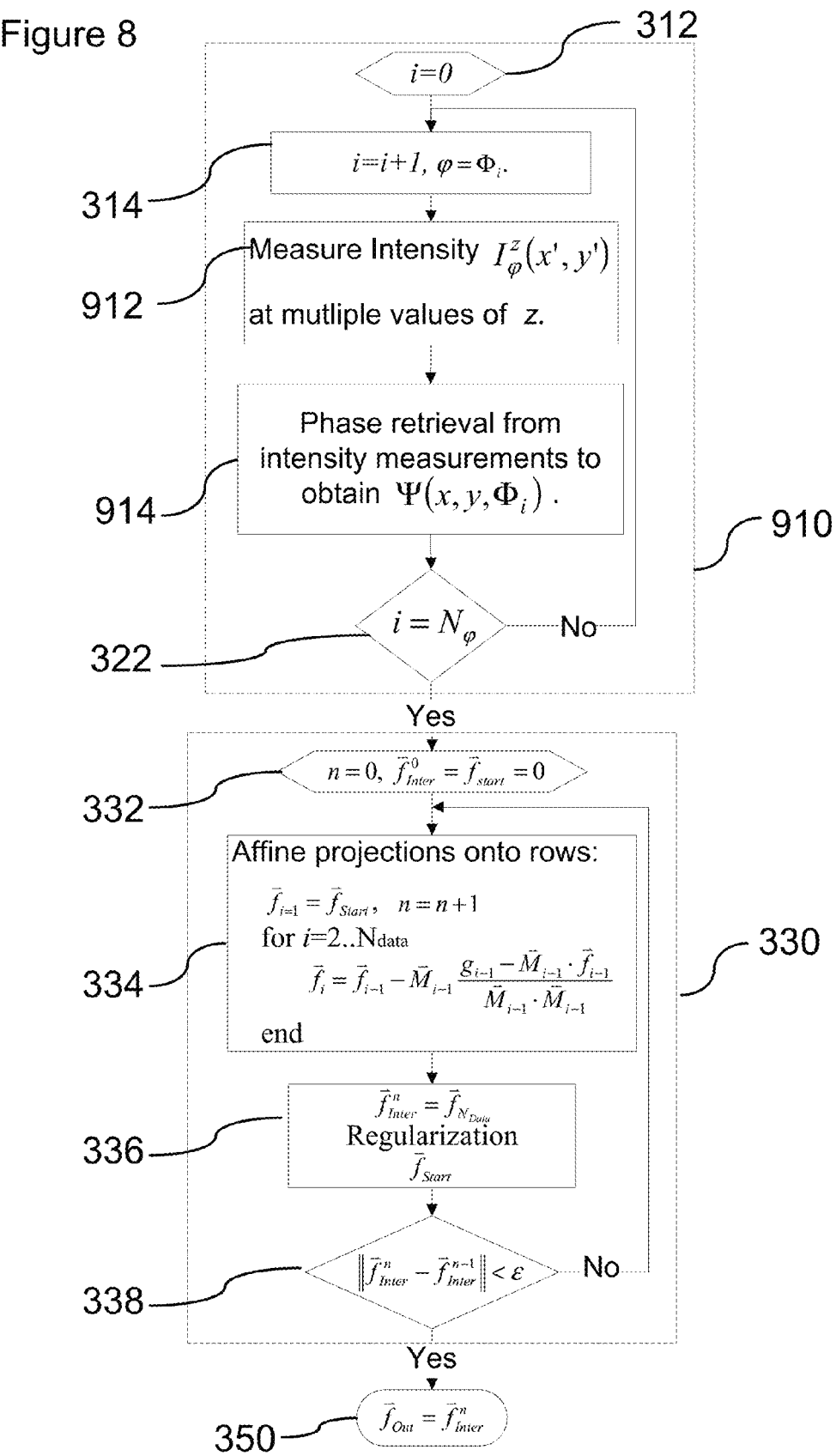
FIG. 8 shows a flowchart diagram of a generalized two-step phase contrast tomography method for retrieving phase projections and iterative image reconstruction of the real part of the index of refraction.

FIG. 8 shows a flowchart for an alternative embodiment of the disclosed inline phase contrast CT method, where the phase retrieval step 914 is generalized to be any of the above-mentioned phase retrieval methods, and the intensity measurement step 912 is generalized to include the measurements required in order to perform the selected phase retrieval method.

Alternative embodiments of the proposed method can use other regularization terms/methods and/or variations on the above mentioned iterative CT reconstruction methods. Some examples of iterative reconstruction methods that can be applied in place of the TV-minimization algorithm include the algebraic reconstruction technique algorithm, the simultaneous iterative reconstruction algorithm, the iterative least squares technique algorithm, and the simultaneous algebraic reconstruction technique algorithm.

In an alternative embodiment, the proposed method can be modified to work for differential phase contrast CT. As described above, in differential phase contrast CT the phase information is derived from measurements of interference patterns created when the radiation beam propagates through multiple diffraction gratings that have been positioned in the X-ray beam path after the image object 212. In this case the differential phase contrast CT measurements and data processing provide the phase information directly, thus eliminating the necessity of a separate phase retrieval step. Therefore, the disclosed two-step phase contrast CT method reduces to a one-step phase contrast CT method when applied to differential phase contrast imaging. In the differential phase contrast adaptation of the proposed phase contrast CT method, the phase projections are obtained directly from the differential phase contrast measurements and data processing. Given the phase projections, the index of refraction image of the image object 212 is created by the iterative image reconstruction loop 330.

Next, a hardware description according to exemplary embodiments is described with reference to FIG. 9. In FIG. 9, the computational hardware includes a CPU 1000 which performs the disclosed two-step phase contrast CT method described above. The process data and instructions may be stored in memory 1002. These processes and instructions may also be stored on a storage medium disk 1004 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the CT processing and reconstruction hardware communicates, such as a server or computer.

Further, the claimed advancements may be provided as a utility application, background daemon, or component of an operating system, or combination thereof, executing in conjunction with CPU 1000 and an operating system such as Microsoft Windows 7, UNIX, Solaris, LINUX, Apple MAC-OS and other systems known to those skilled in the art.

CPU 1000 may be a Xenon or Core processor from Intel of America or an Opteron processor from AMD of America, or may be other processor types that would be recognized by one of ordinary skill in the art. Alternatively, the CPU 1000 may be implemented on an FPGA, ASIC, PLD or using discrete logic circuits, as one of ordinary skill in the art would recognize. Further, CPU 1000 may be implemented as multiple processors cooperatively working in parallel to perform the instructions of the inventive processes described above.

The device in FIG. 9 also includes a network controller 1006, such as an Intel Ethernet PRO network interface card from Intel Corporation of America, for interfacing with a network 1030. As can be appreciated, the network 1030 can be a public network, such as the Internet, or a private network such as an LAN or WAN network, or any combination thereof and can also include PSTN or ISDN sub-networks. The network 1030 can also be wired, such as an Ethernet network, or can be wireless such as a cellular network including EDGE, 3G and 4G wireless cellular systems. The network 1030 can also be WiFi, Bluetooth, or any other wireless form of communication that is known.

The device further includes a display controller 1008, such as a NVIDIA GeForce GTX or Quadro graphics adaptor from NVIDIA Corporation of America for interfacing with display 1010, such as a Hewlett Packard HPL2445w LCD monitor. A general purpose I/O interface 1012 interfaces with a keyboard and/or mouse 1014 as well as a touch screen panel 1016 on or separate from display 1010. General purpose I/O interface also connects to a variety of peripherals 1018 including printers and scanners, such as an OfficeJet or DeskJet from Hewlett Packard.

A sound controller 1020 is also provided in the device, such as Sound Blaster X-Fi Titanium from Creative, to interface with speakers/microphone 1022 thereby providing sounds and/or music.

The general purpose storage controller 1024 connects the storage medium disk 1004 with communication bus 1026, which may be an ISA, EISA, VESA, PCI, or similar, for interconnecting all of the components of the device. A description of the general features and functionality of the display 1010, keyboard and/or mouse 1014, as well as the display controller 1008, storage controller 1024, network controller 1006, sound controller 1020, and general purpose I/O interface 1012 is omitted herein for brevity as these features are known.

While certain embodiments have been described, these embodiments have been presented by way of example only, and are not intended to limit the scope of the inventions. Indeed, the novel methods, apparatuses and systems described herein may be embodied in a variety of other forms; furthermore, various omissions, substitutions and changes in the form of the methods, apparatuses and systems described herein may be made without departing from the spirit of the inventions. The accompanying claims and their equivalents are intended to cover such forms or modifications as would fall within the scope and spirit of the inventions.

The invention claimed is:

1. A method of computer aided imaging, comprising:
obtaining intensity data representing an intensity of radiation at a detector array, wherein a first dataset of the intensity data represents the intensity of the radiation at the detector array after propagating a first distance past an exit plane of an image volume, a second dataset of the intensity data represents the intensity of the radiation at the detector array after propagating a second distance past the exit plane of the image volume, and the first distance is greater than the second distance;
determining, using a phase retrieval method and the intensity data, a phase of the radiation at the exit plane of the image volume; and
reconstructing an image of a real part of an index of refraction of the image volume using an iterative reconstruction algorithm, including performing an affine projection of an image vector onto an affine space determined by a plurality of Radon transforms corresponding to the intensity data, and the image vector represents the real part of the index of refraction of the image volume.

2. The method according to claim 1, wherein the radiation is X-ray radiation.

3. The method according to claim 1, wherein the radiation is a collimated beam having a plurality of rays, each of which is substantially parallel with all other of the plurality of rays of the radiation.

4. The method according to claim 1, wherein the radiation is a cone beam having a plurality of rays, each of which substantially divergent with respect to all other of the plurality of rays of the radiation.

5. The method according to claim 1, wherein the radiation is a fan beam.

6. The method according to claim 1, wherein
the phase retrieval method is one of a transport intensity equation algorithm, a contrast transfer function algorithm, a mixed transport-intensity-equation/contrast-transfer-function algorithm, a Bronnikov algorithm, a modified Bronnikov algorithm, a phase-attenuation duality algorithm, a single material algorithm, a two materials algorithm, a Fourier method with Born approximation method algorithm, and a Fourier method with Rytov approximation algorithm.

7. The method according to claim 1, wherein
the reconstruction algorithm is one of an algebraic reconstruction technique algorithm, a total variation minimization method algorithm, a simultaneous iterative reconstruction algorithm, an iterative least squares technique algorithm, and a simultaneous algebraic reconstruction technique algorithm.

8. An apparatus for determining an image, comprising:
a processing circuit configured to
obtain intensity data representing an intensity of radiation at a detector array, wherein a first dataset of the intensity data represents the intensity of the radiation at the detector array after propagating a first distance past an exit plane of an image volume, a second dataset of the intensity data represents the intensity of the radiation at the detector array after propagating a second distance past the exit plane of the image volume, and the first distance is greater than the second distance;
determine, using a phase retrieval method and the intensity data, a phase of the radiation at the exit plane of the image volume; and
reconstruct an image of a real part of an index of refraction of the image volume using an iterative reconstruction algorithm, including performing an affine projection of an image vector onto an affine space determined by a plurality of Radon transforms corresponding to the intensity data, and the image vector represents the real part of the index of refraction of the image volume.

9. The apparatus according to claim 8, wherein the processing circuitry is further configured to reconstruct the image of the real part of the index of refraction using the iterative reconstruction algorithm, wherein the iterative reconstruction algorithm is a total variation minimization algorithm.

10. The apparatus according to claim 8, wherein the processing circuitry is further configured to reconstruct the image of the real part of the index of refraction using the iterative reconstruction algorithm, wherein the iterative reconstruction algorithm is one of an algebraic reconstruction technique algorithm, a simultaneous iterative reconstruction algorithm, an iterative least squares technique algorithm, and a simultaneous algebraic reconstruction technique algorithm.

11. The apparatus according to claim 8, wherein the processing circuitry is further configured to determine the phase of the radiation at the exit plane the image volume, wherein the phase retrieval method is one of a transport intensity equation algorithm, a contrast transfer function algorithm, a mixed transport-intensity-equation/contrast-transfer-function algorithm, a Bronnikov algorithm, a modified Bronnikov algorithm, a phase-attenuation duality algorithm, a single material algorithm, a two materials algorithm, a Fourier method with Born approximation method algorithm, and a Fourier method with Rytov approximation algorithm.

* * * * *